United States Patent
Almulhim

(10) Patent No.: US 11,944,345 B1
(45) Date of Patent: Apr. 2, 2024

(54) RADIALLY EXPANDING TROCAR FOR LAPAROSCOPIC CHOLECYSTECTOMY

(71) Applicant: KING FAISAL UNIVERSITY, Al-Ahsa (SA)

(72) Inventor: Abdulrahman Saleh Almulhim, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 50 days.

(21) Appl. No.: 17/972,082

(22) Filed: Oct. 24, 2022

(51) Int. Cl.
*A61B 17/34* (2006.01)
*A61B 17/32* (2006.01)
*A61B 17/00* (2006.01)

(52) U.S. Cl.
CPC .. *A61B 17/3421* (2013.01); *A61B 17/320016* (2013.01); *A61B 17/3498* (2013.01); *A61B 2017/00818* (2013.01); *A61B 2017/00907* (2013.01); *A61B 2017/3419* (2013.01); *A61B 2017/3486* (2013.01)

(58) Field of Classification Search
CPC ............ A61B 17/3439; A61B 17/3421; A61B 17/3498; A61B 17/320016; A61B 17/6417; A61B 2017/3419; A61B 2017/3486; A61M 25/1006
See application file for complete search history.

(56) References Cited

U.S. PATENT DOCUMENTS

| | | | |
|---|---|---|---|
| 5,256,149 A * | 10/1993 | Banik | A61B 17/3421 604/164.01 |
| 5,295,994 A * | 3/1994 | Bonutti | A61M 5/3286 604/164.11 |
| 5,681,324 A | 10/1997 | Kammerer et al. | |
| 5,707,359 A | 1/1998 | Bufalini | |
| 2005/0192608 A1* | 9/2005 | Moreno | A61B 17/3462 606/167 |
| 2012/0046525 A1 | 2/2012 | Russell et al. | |
| 2014/0276869 A1* | 9/2014 | Tatsumi | A61B 17/3421 606/90 |
| 2015/0073333 A1 | 3/2015 | Knowles | |
| 2015/0209078 A1* | 7/2015 | Nevler | A61B 17/3439 604/159 |

FOREIGN PATENT DOCUMENTS

CN 209951306 1/2020

* cited by examiner

Primary Examiner — Diane D Yabut
(74) Attorney, Agent, or Firm — Nath, Goldberg & Meyer; Richard C. Litman

(57) ABSTRACT

A radially expanding trocar for laparascopic cholecystectomy includes an awl, a cannula, a seal, and a valve connected to the seal. A balloon extends within the cannula. A lower portion of the cannula can be made from any suitable, expandible material. An inflation tube can be in fluid communication with the interior of balloon and the valve to allow air or water into the balloon. Inflating the balloon can cause the balloon to press against an inner surface of the peripheral wall of the cannula, expanding the peripheral wall and increasing a diameter of the cannula. The balloon can be deflated to release the pressure on the peripheral wall and decrease the diameter of the cannula to its original size, e.g., 12 mm.

9 Claims, 3 Drawing Sheets

RADIALLY EXPANDING TROCAR FOR LAPAROSCOPIC CHOLECYSTECTOMY

BACKGROUND

1. Field

The disclosure of the present patent application relates to laparoscopic surgical tools and, particularly, to a laparascopic surgical tool for gallbladder extraction.

2. Description of the Related Art

Laparoscopic surgical techniques have been developed in order to avoid large skin incisions associated with traditional surgery. The abdomen or surgical space is inflated to enlarge the cavity and allow for the surgical procedure. A small incision provides an access port for an endoscope and surgical instruments. These minimally invasive surgical procedures involve percutaneously accessing an internal surgical site with a small-diameter trocar, generally 12 mm in diameter.

One particular laparoscopic surgical procedure which has become relatively common in clinical application is the "laparoscopic cholecystectomy". The laparoscopic cholecystectomy generally requires insertion of a laparoscope through the primary periumbilical portal and various forceps and other operative instruments through secondary portals. The gallbladder is then grasped with forceps, clips are placed on the cystic artery and bile duct and the gallbladder is subsequently excised.

Thereafter, the laparoscope is extracted from the primary portal and relocated to a secondary portal. Forceps are then utilized to move the gallbladder to a position adjacent the periumbilical incision and to exteriorize the neck of the gallbladder through the periumbilical incision. If possible, the entire body of the gallbladder is then extracted through the periumbilical incision. Such extraction of the gallbladder may be complicated, however, in instances where the diseased stone-containing gallbladder is too large to pass through the relatively small (e.g. 1 cm) periumbilical incision.

In such instances, it is current practice to insert forceps through the exteriorized neck of the gallbladder to attempt to manually crush and remove some or all of the gallstones. Such manual crushing of the gallstones is time-consuming and may well result in perforation of the gallbladder wall. Alternatively, the surgeon may elect to enlarge the small periumbilical incision in order to remove the entire body of the stone containing gallbladder. Such enlargement of the incision is undesirable and may lead to increased postoperative discomfort.

In view of the problems associated with removing tissue, organs, or other material through a relatively small laparoscopy incision, there exists a need in the art for an instrument which may be passed into and removed from the standard laparoscopy incision. Thus, a radially expanding trocar for laparascopic cholecystectomy solving the aforementioned problems is desired.

SUMMARY

A radially expanding trocar for laparascopic cholecystectomy includes an awl, a cannula, a seal, and a valve connected to the seal. A balloon extends within the cannula. A lower portion of the cannula can be made from a suitable, expandable material. An inflation tube can be in fluid communication with the interior of balloon and the valve to allow air or water into the balloon. Inflating the balloon can cause the balloon to press against an inner surface of the lower peripheral wall of the cannula, expanding the lower peripheral wall and increasing a diameter of the lower end of the cannula. Once the gallbladder is within the cannula, the balloon can be deflated to release the pressure on the peripheral wall and decrease the diameter of the cannula to its original size, e.g., 12 mm. In use, the cannula can be inserted into an incision made in the abdomen. The lower portion of the cannula can then be expanded by inflating the balloon. The resulting increased diameter of the cannula can accommodate an enlarged gallbladder. Subsequent contraction of the cannula peripheral wall can compress the gallbladder and permit the cannula to be removed from the abdomen without enlarging the original abdominal incision.

These and other features of the present invention will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
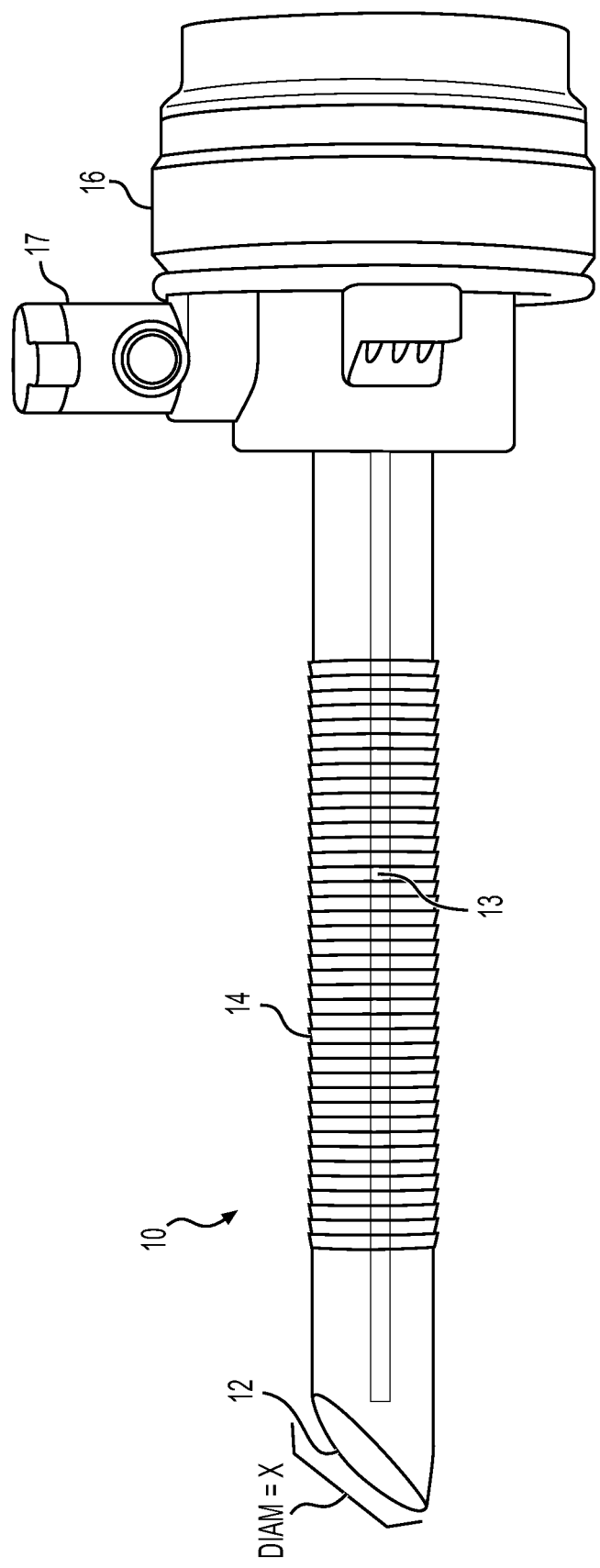
FIG. 1 is a perspective view of the radially expanding trocar for laparascopic cholecystectomy according to the present teachings.
Figure 2:
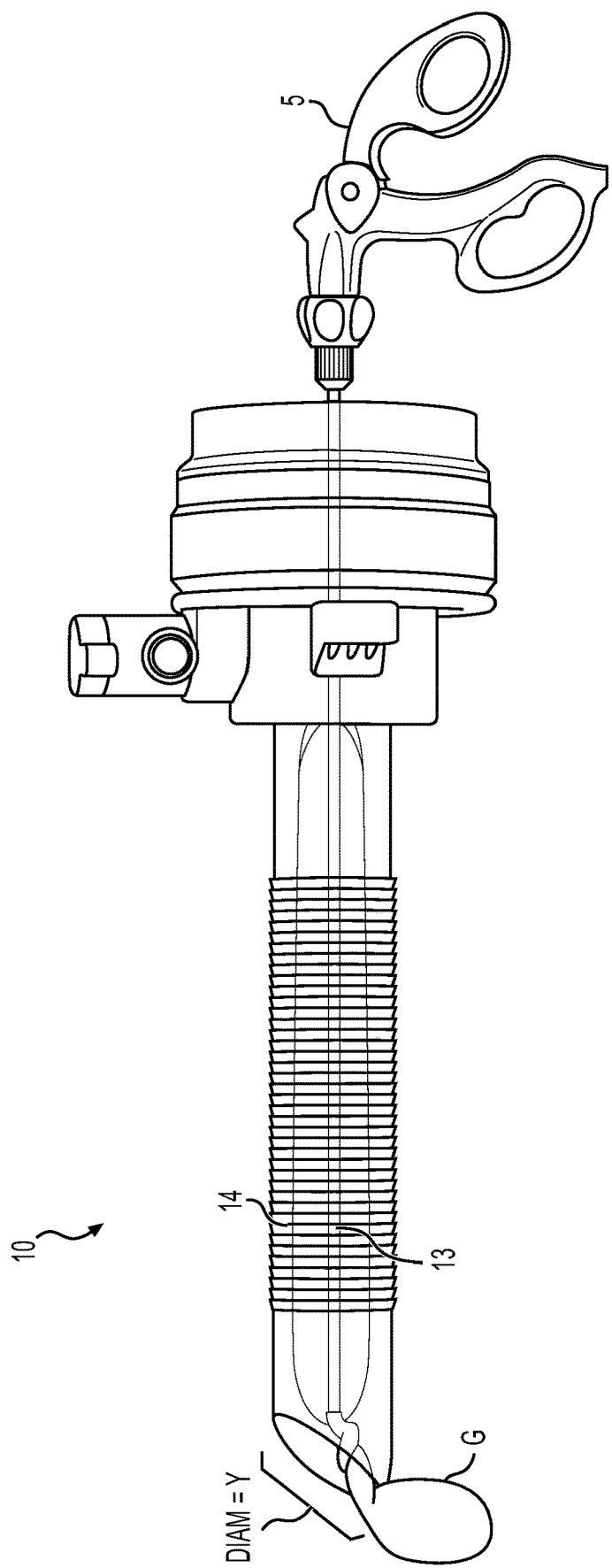
FIG. 2 is a perspective view of the radially expanding trocar for laparascopic cholecystectomy according to the present teachings, showing the gallbladder extracted with a surgical instrument.
Figure 3:
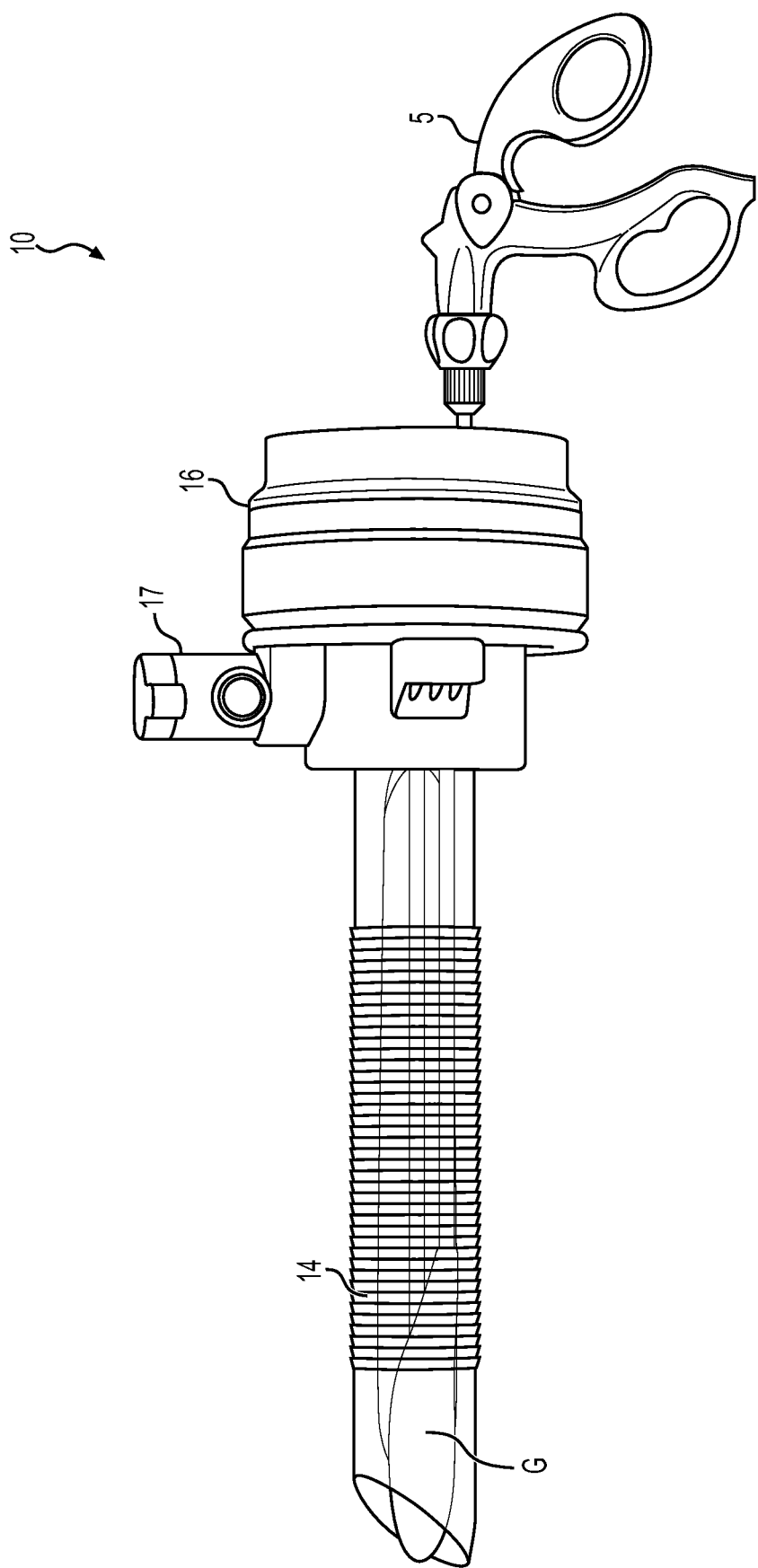
FIG. 3 is a perspective view of the radially expanding trocar for laparascopic cholecystectomy according to the present teachings, showing the extracted gallbladder completely disposed in the cannula.

As shown in FIG. 1, a radially expanding trocar for laparascopic cholecystectomy, generally designated as 10, includes an awl 12, a cannula 14, a seal 16, and a valve 17 connected to the seal 16. The awl 12 defines a lower end of the trocar 10 and the seal defines an upper end of the trocar 12. A balloon 13 extends within the cannula 14. A lower portion of the cannula 14 can be made from a suitable, expandible material. An inflation tube can be in fluid communication with the interior of balloon 13 and the valve 17 to allow air or water into the balloon 13. Inflating the balloon 13 can cause the balloon 13 to press against an expandible, inner surface of the peripheral wall of the cannula 14 to increasing a diameter of the lower portion of the cannula 14. In an embodiment, upon inflation of the balloon 13, the diameter at the lower portion of the cannula 14 can be increased from 12 mm to 18 mm. The balloon 13 can be deflated to release the pressure on the peripheral wall and decrease the diameter of the cannula 14 to its original size, e.g., 12 mm.

As is generally known, the seal 16 is configured to receive a surgical instrument 5 while preventing gases to escape therethrough. The valve 17 can configured to selectively provide air to the balloon 13 and permit release of air therefrom.

In use, the awl 12 can be fully inserted through an incision in the abdomen. A surgical instrument 5 can then be inserted into the abdomen through the trocar 10. The balloon 13 can then be inflated to increase the diameter of a lower portion of the cannula 14, e.g., the portion of the cannula beneath the incision. Once the balloon 13 is inflated, the diameter of the lower portion of the cannula 14 is increased, for example, from about 12 mm to about 18 mm. The balloon 13 can remain expanded while the surgical instrument 5 is manipulated within the abdomen to extract the gallbladder G. Once the gallbladder G is pulled into the trocar 10, the balloon 13 can be deflated by manipulating valve 17. Deflation of the balloon 13 permits the peripheral wall of the balloon 13 to contract and, thereby, decrease the diameter of the cannula 14 and compress the gallbladder G. Once the diameter of the cannula 14 has resumed its original size, the trocar 10 can be removed from the abdomen.

A lower portion of the cannula 14 can be formed from a suitable expandible material. In an embodiment, the cannula 14 is formed from a transparent material such that the interior of the cannula 14 is visible through the cannula 14. This allows the user to view the surgical instrument 5 inserted into the cannula 14 and the gallbladder G once it is introduced into the cannula 14. Various conventional endoscopic surgical instruments, surgical staplers, sutures, needles, pharmaceuticals, tissue, tissue samples, drug delivery devices, electrosurgical devices, electrodes, etc., can be inserted through the trocar cannula and maneuvered to the target surgical site where conventional endoscopic surgical techniques are utilized.

The cannula 14 may be constructed using conventional manufacturing techniques from any conventional, medical grade material which allows the interior of cannula to be visible through the cannula. Transparent, plastic materials such as polycarbonate, acrylates, urethanes, polyvinylchlorides, and copolymers thereof as well as clear composite resins or co-extruded resin systems and the like can be used. Transparent is defined to mean the ability to pass light through a material so that it is possible to see through the material.

The peripheral wall of the trocar cannula 14 can be sufficiently thick to effectively provide the required mechanical strength, yet allow expansion of the peripheral wall upon expansion of the balloon 13 within the cannula 14 and contraction when the balloon 13 is deflated. The wall thickness will depend upon the diameter of the cannula and its length. Mechanical strength is defined to mean those mechanical characteristics conventionally required for effective functioning of a trocar including bending strength, resistance to buckling, shear strength, maximum allowable deflection under maximum load, thermal expansion and contraction, shell strength, pressure rating, safety factors and the like.

The awl can be configured to penetrate the abdominal wall. For example, the awl can be formed from metal or a sharpened plastic. If the awl is sharp, the trocar can include a spring-loaded mechanism, as is known in the art, that withdraws the sharp tip after it passes through the abdominal wall. Alternatively, the awl can be non-bladed and the cannula can be used with an obturator, as is known in the art.

It is to be understood that the radially expanding trocar for laparascopic cholecystectomy is not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A radially expanding trocar for laparoscopic cholecystectomy, comprising:
   a cannula having a peripheral wall, a lower portion of the peripheral wall being expandible;
   an inflatable balloon extending within the cannula along an entire length of the cannula wherein the inflatable balloon while inflating applies an external pressure against an inner surface of the peripheral wall;
   an awl at a lower end of the cannula;
   a seal at an opposing upper end of the cannula; and
   a valve connected to the seal and in communication with the balloon.

2. The radially expanding trocar for laparoscopic cholecystectomy as recited in claim 1, wherein a diameter of the cannula is 18 mm in an expanded state and 12 mm in a non-expanded state.

3. The radially expanding trocar for laparoscopic cholecystectomy as recited in claim 1, wherein the awl includes a sharp blade.

4. The radially expanding trocar for laparoscopic cholecystectomy as recited in claim 1, further comprising a surgical instrument removably extending through the seal.

5. The radially expanding trocar for laparoscopic cholecystectomy as recited in claim 1, wherein the peripheral wall of the cannula is transparent.

6. A radially expanding trocar for laparoscopic cholecystectomy, comprising:
   a cannula having a transparent peripheral wall, at least a portion of the peripheral wall being expandible;
   an inflatable balloon extending within the cannula along an entire length of the cannula wherein the inflatable balloon while inflating applies an external pressure against an inner surface of the peripheral wall;
   an awl at a lower end of the cannula;
   a seal at an opposing upper end of the cannula; and
   a valve connected to the seal and in communication with the balloon.

7. The radially expanding trocar for laparoscopic cholecystectomy as recited in claim 6, wherein a diameter of the cannula is 18 mm in an expanded state and 12 mm in a non-expanded state.

8. The radially expanding trocar for laparoscopic cholecystectomy as recited in claim 6, wherein the awl includes a sharp blade.

9. The radially expanding trocar for laparoscopic cholecystectomy as recited in claim 6, further comprising a surgical instrument removably extending through the seal.

* * * * *